United States Patent
Horna Tomas et al.

(10) Patent No.: US 9,587,216 B2
(45) Date of Patent: Mar. 7, 2017

(54) CELL CULTURE METHOD AND SYSTEM

(71) Applicant: AGLARIS CELL S.L., Getafe (ES)

(72) Inventors: David Horna Tomas, Getafe (ES); Miguel Costa Ferrando, Madrid (ES)

(73) Assignee: Aglaris Cell S.L., Getafe (ES)

( * ) Notice: Subject to any disclaimer, the term of this patent is extended or adjusted under 35 U.S.C. 154(b) by 0 days.

(21) Appl. No.: 14/410,310

(22) PCT Filed: Jun. 13, 2013

(86) PCT No.: PCT/EP2013/062293
§ 371 (c)(1),
(2) Date: Dec. 22, 2014

(87) PCT Pub. No.: WO2013/186318
PCT Pub. Date: Dec. 19, 2013

(65) Prior Publication Data
US 2015/0159128 A1  Jun. 11, 2015

(30) Foreign Application Priority Data
Jun. 14, 2012 (ES) .................. 201230933

(51) Int. Cl.
| | |
|---|---|
| *C12M 1/34* | (2006.01) |
| *C12M 1/00* | (2006.01) |
| *C12M 1/26* | (2006.01) |
| *C12M 1/12* | (2006.01) |

(52) U.S. Cl.
CPC ............ *C12M 41/46* (2013.01); *C12M 29/10* (2013.01); *C12M 33/00* (2013.01); *C12M 37/00* (2013.01); *C12M 41/36* (2013.01)

(58) Field of Classification Search
None
See application file for complete search history.

(56) References Cited

U.S. PATENT DOCUMENTS

| | | | |
|---|---|---|---|
| 5,202,254 A * | 4/1993 | Amiot ................... | C12M 23/58 435/297.4 |
| 7,507,579 B2 | 3/2009 | Boccazzi et al. | |
| 7,790,444 B2 | 9/2010 | Ahluwalia et al. | |
| 2002/0214314 | 10/2004 | Srienc | |
| 2005/0054101 A1 | 3/2005 | Felder et al. | |
| 2007/0134790 A1 | 6/2007 | Gould et al. | |
| 2008/0299539 A1 | 12/2008 | Lee et al. | |
| 2010/0190963 A1* | 7/2010 | Moya .................... | C12M 23/20 530/387.3 |
| 2012/0009559 A1 | 1/2012 | Felder et al. | |
| 2012/0034596 A1* | 2/2012 | Seidl ..................... | C12M 41/48 435/3 |
| 2012/0122208 A1 | 5/2012 | Fisher et al. | |

FOREIGN PATENT DOCUMENTS

| | | |
|---|---|---|
| DE | 19952847 | 4/2001 |
| DE | 102010026369 | 1/2012 |
| EP | 1279728 | 1/2003 |
| EP | 1548099 | 6/2005 |
| EP | 2404991 | 1/2012 |
| WO | 0125396 | 4/2001 |
| WO | 03089567 | 10/2003 |
| WO | 2010121601 | 10/2010 |
| WO | 2011135339 | 11/2011 |

OTHER PUBLICATIONS

"International Search Report for PCT/IN2013/062293 dated Aug. 22, 2013".

* cited by examiner

*Primary Examiner* — Suzanne M Noakes
*Assistant Examiner* — Stephen Chong
(74) *Attorney, Agent, or Firm* — Kramer Amado P.C.

(57) ABSTRACT

The invention is comprised within automated devices for cell culture. The invention relates to a cell culture method and system which allows modifying in a controlled manner the density and the number of cells in a culture. Specifically, the present invention relates to an iterative method the number of iteration steps of which is modified depending on the demand for the density and the number of cells necessary for the culture duration.

10 Claims, 3 Drawing Sheets

CELL CULTURE METHOD AND SYSTEM

OBJECT OF THE INVENTION

The invention is comprised within automated devices for cell culture. The invention relates to a cell culture method and system which allow modifying in a controlled manner the density and the number of cells in a culture. Specifically, the present invention relates to an iterative method the number of iteration steps of which is modified depending on the demand for the density and the number of cells necessary for the culture duration.

BACKGROUND OF THE INVENTION

Automated bioreactors manufactured by companies such as Caridian BCT, PAN-systech, or the "wave bioreactor" of General Electric, can be found in the state of the art.

International patent application WO 2010/121601 A2 of PAN-systech shows an automatic bioreactor for multi-well cell cultures.

However, the devices and methods known in the state of the art have the technical problem of not being versatile enough in the sense that they do not allow performing multiples cell expansions within one and the same bioreactor by demand, leading to the inability to control and to precisely modify cell density and the total number of cells as it advances into the amplification process, and to a narrow range of values in which work can be performed.

These limitations greatly complicate the use of bioreactors for cell therapy.

DESCRIPTION OF THE INVENTION

A cell culture method according to claim 1 and a cell culture system according to claim 10 have been developed to solve the problems considered in the state of the art. The dependent claims define particular embodiments of the invention.

The first inventive aspect of the invention consists of the mentioned cell culture method and is characterized in that it is implemented in a system comprising:
  at least one device suitable for culturing cells, the device comprising:
    at least one bioreactor chamber comprising at least one inner surface suitable for cell culture,
    fluid inlet-outlet means, and
    at least one pre-chamber in connection with the at least one bioreactor chamber comprising an inlet for introducing cells,
and in that it comprises the following steps:
  a) filling the pre-chamber with a culture medium under initial physicochemical conditions with a predetermined volume of liquid,
  b) introducing cells through the cell inlet for introducing cells of the pre-chamber,
  c) passing the culture medium with the cells to the at least one bioreactor chamber,
  d) leaving the cells to settle and leaving them to stand for a predetermined time until they adhere to the at least one inner surface suitable for cell culture the physicochemical properties of which cause it to behave in such a way that it favors cell adhesion under one or several initial physicochemical conditions,
  e) circulating culture medium through the device and through the fluid inlet-outlet means f) once a target number of cells is obtained or a critical density is reached in the at least one bioreactor chamber used for the culture, changing at least one of the initial physicochemical conditions of the culture medium to modified physicochemical conditions under which cell adhesion is prevented, such that the volume remaining within the device under modified physicochemical conditions is located in the chambers which have been used for cell amplification,
  g) transferring the culture medium with the cells to the pre-chamber, and
  if the target number of cells has been reached, introducing an additional volume of culture medium in the pre-chamber and extracting the culture medium with the cells in suspension through outlet means, or
  if the target number of cells has not been reached, introducing additional culture medium in the pre-chamber and repeating the steps starting from step c).

The object of the method of the invention is to allow modifying in a controlled manner the density and the number of cells in a culture. Specifically, the invention relates to an iterative method the number of iteration steps of which is modified depending on the demand for the density and the number of cells necessary for the culture duration.

Specifically, the iterative method starts with the introduction of culture medium in the pre-chamber of the device such that the medium is separated from the at least one bioreactor chamber. The cells object of amplification are then introduced and the entire mixture formed by the medium and the cells is then transferred to the at least one culturing chamber through the connection between the pre-chamber and the chamber. Throughout this document, the terms "cell amplification" and "cell culture" are understood as synonyms. On the other hand, when mention is made of physicochemical conditions, it refers to the particular conditions of at least one parameter, such as temperature, pH level or saline concentration or the like.

To successfully perform a cell amplification process, it is convenient for the cells to adhere to a surface where cell division processes start. To that end, the next step of the method comprises leaving the cells to stand such that they adhere to an inner surface of the device in the at least one bioreactor chamber suitable for cell culture. This surface is adapted for changing its suitability for cell adhesion depending on the value of at least one of the initial physicochemical conditions, for example, the temperature, the pH or the saline concentration, either due to the nature of the material with which it was manufactured, or to the fact that it is coated with a gel or a product the properties of which change with the at least one selected initial physicochemical condition, for example, the temperature. The at least one of the initial physicochemical conditions of the culture medium, for example, a first temperature T1, is selected such that the characteristic of the inner surface at that temperature is such that it allows cell adhesion.

When the cells have adhered to the surface, a continuous flow of culture medium is started under initial physicochemical conditions. This continuous flow provides the cells with necessary nutrients such as amino acids and vitamins in a continuous and renewed manner so that the growth rate is constant and optimum. Therefore, cell amplification is carried out until obtaining a specific cell density, from which the quality of the culture is not as required, or a target number of cells.

Once this density or this target number of cells has been obtained, at least one of the initial physicochemical conditions of the medium is changed to modified physicochemical conditions, for which the surface suitable for cell culture has a physicochemical characteristic allowing the cells to again be in suspension in the medium.

In a non-limiting embodiment, the way of changing at least one of the physicochemical conditions is by emptying the bioreactor chambers of culture medium at temperature T1 and then filling the culturing chambers containing cells with medium at temperature T2. In a particular example, the volume of the medium which is introduced in each chamber under the modified physicochemical conditions is the volume which has been introduced in each chamber at the start of the process. The cells under these modified physicochemical conditions thus detach from the surfaces suitable for cell adhesion. The liquid medium with the cells in suspension is then transferred to the pre-chamber.

Once the liquid medium under modified physicochemical conditions and the cells in suspension are in the pre-chamber, there are two options:
  either a larger amount of cells is needed, in which case more culture medium is added to the pre-chamber and all the steps are repeated starting from step c) until reaching the target number of cells, or
  the target number of cells has been reached, in which case the liquid medium with the cells in suspension is extracted from the pre-chamber.

The method provides the technical advantage of being able to control in vivo the number of cells required throughout the method, with the subsequent versatility of being able to modify the final target number of cells in accordance with the requirements of the applied method.

In a second inventive aspect, the present invention relates to a cell culture system comprising:
  at least one device suitable for culturing cells, the device comprising:
    at least one bioreactor chamber comprising at least one inner surface suitable for cell culture,
    fluid inlet-outlet means
    at least one pre-chamber in connection with the at least one bioreactor chamber comprising an inlet for introducing cells.

The system can also be used in a versatile manner for different uses, for example, for cell reprogramming or cell expansion by means of exchanging detachable devices each of which is adapted for the type of work that it performs.

All the features described in this specification (including the claims, description and drawings) can be combined in any combination, except the combinations of such mutually exclusive features.

DESCRIPTION OF THE DRAWINGS

To complement the description that will be made below and for the purpose of aiding to better understand the features of the invention according to a preferred practical embodiment thereof, a set of drawings is attached as an integral part of said description in which the following has been depicted with an illustrative and non-limiting character:

FIG. 2.1, FIG. 2.2, FIG. 2.3 and FIG. 2.4 show a particular example of a sequence of steps of the method according to the invention applied to a particular example of the system.

DETAILED DESCRIPTION OF THE INVENTION

Cell Culture System

The cell culture system proposed by the invention is a system comprising:
  at least one device (1) suitable for culturing cells, the device (1) comprising:
    at least one bioreactor chamber (2) comprising at least one inner surface (22, 3, 39) suitable for cell culture,
    fluid inlet-outlet means (13, 14, 15, 17, 18, 19, 23, 24),
    at least one pre-chamber (4) in connection with the at least one bioreactor chamber (2) comprising an inlet (5) for introducing cells.

The culture medium is contained in a chamber (7) for containing cell culture medium which is kept at the desired pressure condition, temperature condition, pH condition, oxygen level and carbon dioxide level. To that end, in one embodiment, this chamber (7) for containing culture medium is provided with sensors for these conditions and is connected to an oxygen cylinder, to a carbon dioxide cylinder, to a NaOH dispenser, to a nitrogen cylinder controlling the pressure (all these connections with their corresponding valves) and, in a particular example, to a heat exchanger (11) which allows changing the temperature, the particular physicochemical condition in this example.

Figure 1:
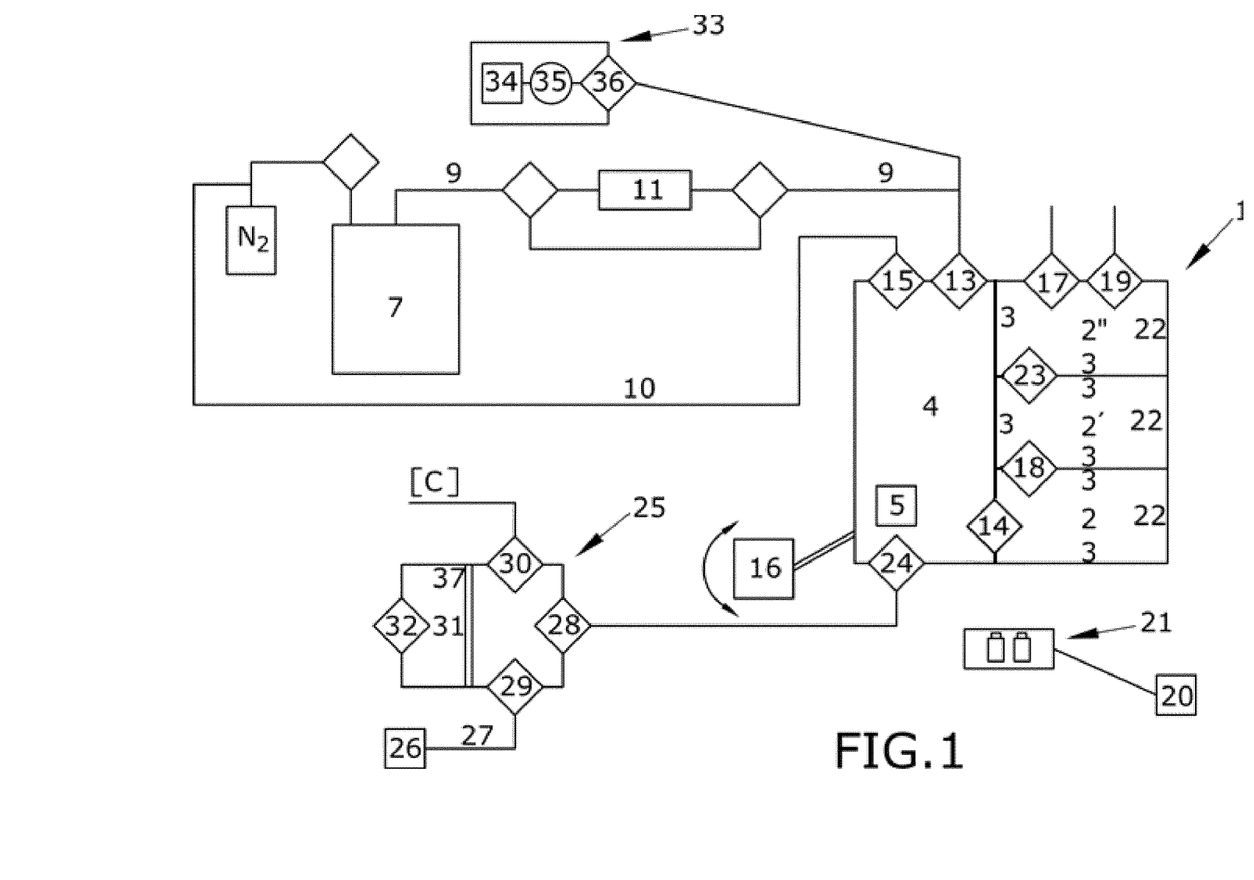
FIG. 1 shows an embodiment of a system according to the invention.

The chamber (7) for containing cell culture medium is in connection with a device (1) by means of at least one first conduit (9) for transporting culture medium; at least one second conduit (10) for transporting gases which further connects a gas feed system, $N_2$ in the embodiment of FIG. 1, with the device (1). These at least one first and second transport conduits (9, 10), in the example depicted in FIG. 1, also have valves for controlling the flow of the medium and of the gas; one of the valves for controlling the flow of the medium allows selecting, in the example of FIG. 1 where the at least one of the initial physicochemical conditions that changes is the temperature, between two alternative paths for the culture medium, one of which goes through a heat exchanger (11) making it possible to condition the temperature thereof before reaching the device (1).

Advantageously, in a particular embodiment of the system according to the invention, the device (1) is detachable and provides the system with an element that can be acquired independently and be adapted to different cell culture, such as for example, mammalian cells, bacteria cells, etc. Therefore, the device adapts the system for different purposes by only exchanging the detachable device (1) depending on the method to be performed.

Cell Culture Method

The method presented by the invention is characterized in that it is implemented in a system comprising:
  at least one device (1) suitable for culturing cells, the device (1) comprising:
    at least one bioreactor chamber (2) comprising at least one inner surface (22, 3, 39) suitable for cell culture,
    fluid inlet-outlet means (13, 14, 15, 17, 18, 19, 23, 24),
    at least one pre-chamber (4) in connection with the at least one bioreactor chamber (2) comprising an inlet (5) for introducing cells,
and in that it comprises the following steps:
  a) filling the pre-chamber (4) with a culture medium under initial physicochemical conditions with a predetermined volume of liquid, the pre-chamber (4) being positioned such that the culture medium does not pass to the at least one bioreactor chamber (2), b) introducing cells through the cell inlet (5) for introducing cells of the pre-chamber (4), c) passing the culture medium with the cells to the at least one bioreactor chamber (2), d) leaving the cells to settle and leaving them to stand for a predetermined time until they adhere to the at least one inner surface (22, 3, 39) suitable for cell culture the physicochemical properties of which cause it to behave in such a way that it favors cell adhesion under several initial physicochemical conditions, e) circulating liquid through the device (1) and through the fluid inlet-outlet means (13, 14, 15, 17, 18, 19, 23, 24) until obtaining a target number of cells or until reaching a critical density in the at least one bioreactor chamber (2) filled with culture medium, f) once a target number of cells is obtained or a critical density is reached in the at least one bioreactor chamber (2, 2', 2") used for the culture, changing at least one of the initial physicochemical conditions of the culture medium to modified physicochemical conditions under which cell adhesion is prevented, such that the volume remaining within the device (1) under modified physicochemical conditions is located in the bioreactor chambers (2, 2', 2") which have been used for cell amplification, g) passing the culture medium with the cells to the pre-chamber (4), and if the target number of cells has been reached, extracting the culture medium with the cells in suspension through outlet means (24), or if the target number of cells has not been reached, introducing additional culture medium in the pre-chamber (4) and repeating the steps starting from step c).

In an embodiment in the first step, only one bioreactor chamber (2) for cell culture is filled up. In a particular example, the pre-chamber (4) of the device (1) is filled with culture medium through a valve (13), as observed in FIGS. 1 and 2. The amount of culture medium that accumulates in the pre-chamber (4) before closing this valve (13) is usually, but no always, equal to the volume of the first bioreactor chamber (2). In this example, only one bioreactor chamber (2) is filled up in the first step. Before filling the bioreactor chamber, the cells are introduced in the pre-chamber (4) through the inlet (5) for introducing cells so that they are in suspension in the culture medium.

In the particular example of FIG. 1, the culture medium with the cells in suspension is passed to the first bioreactor chamber (2) by means of moving the device (1) and introducing nitrogen through the valve (15) since it is inert for the cells. The device (1) is moved by means of a mechanism (16) for moving the device (1). The particular example of FIG. 1 depicts a device (1) with three bioreactor chambers (2, 2', 2"):

In a particular example, the pre-chamber (4) is in connection with the first bioreactor chamber (2) by means of a second valve (14) which is located in the part of the wall close to the corner of the pre-chamber separating the chambers.

Figure 22:
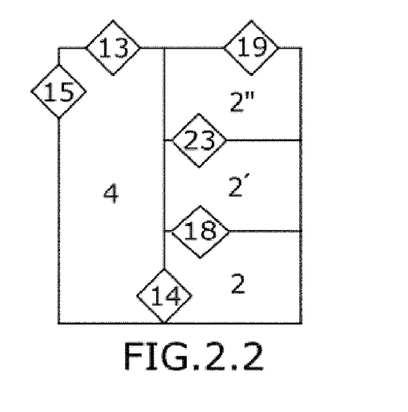

In the particular example depicted in FIG. 2.2, the device (1) changes its position from horizontal to vertical, vertical position being understood as that whereby the longer wall of the device (1) is located in a vertical direction, and horizontal position being understood as that whereby the longer wall of the device (1) is located in a horizontal direction, by means of a mechanism (16) for moving the device (1), as seen in FIG. 1, which in this particular embodiment is a motor capable of transferring a rotational movement.

The second valve (14) is in a position such that the culture medium with the cells in suspension is located in the pre-chamber (4) at a height equal to or greater than the valve, therefore being able to pass through same. To facilitate the fluid medium transfer between the pre-chamber (4) and the bioreactor chamber (2), in a particular example, the pre-chamber (4) comprises a gas inlet valve (15) connected to a nitrogen cylinder and the last bioreactor chamber (2"), which in this example is the third bioreactor chamber, comprises a second gas outlet valve (19). Therefore, the transfer of the culture medium with the cells in suspension is facilitated by injecting, in this particular case, nitrogen since it is inert for the cells.

Figure 23:
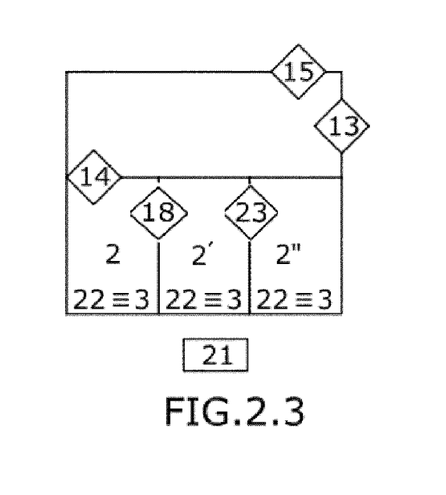

Once the culture medium with the cells in suspension has been passed to the first bioreactor chamber (2), the mechanism (16) for moving the device (1) moves the device (1) to a position such that the second valve (14) between the pre-chamber (4) and the first bioreactor chamber (2) is, in this particular example, at a height equal to or greater than that of the culture medium with the cells in suspension, and the culture medium is thus located in the bioreactor chamber (2) without the possibility of having an escape route towards the pre-chamber (4). This step is shown in FIG. 2.3.

Figure 3:
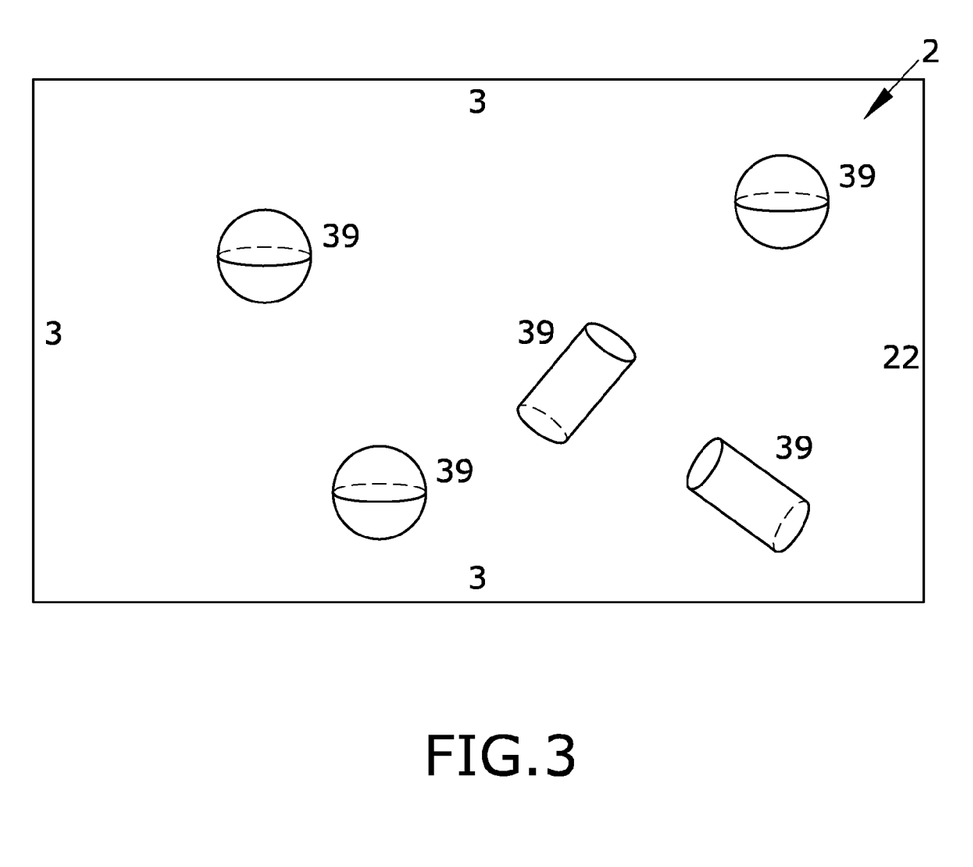
FIG. 3 shows a particular example of a bioreactor chamber (2) with additional surfaces for cell adhesion (39).
Figure 21:
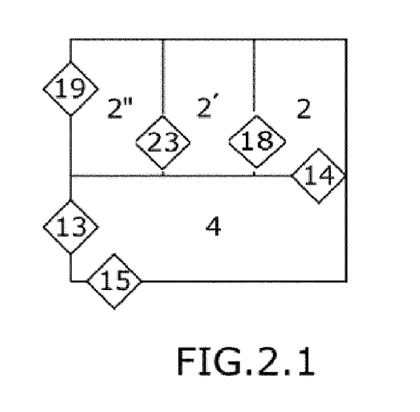

In an embodiment shown in FIG. 3, the bioreactor chamber (2) internally comprises a series of additional surfaces for cell adhesion (39), which can be of spherical or tubular shape, among other shapes, so that the useful surface for culture is greater than that allowed by the inner surfaces (22, 3) suitable for cell culture of the bioreactor chamber (2). In a particular example, the additional surfaces for cell adhesion (39) are a plurality of biomolecules, preferably proteins, peptides or biologically active synthetic molecules comprised in at least one inner surface of the device.

In a particular embodiment, to make adhesion possible, the additional surfaces for cell adhesion (39) and the inner surfaces (22, 3) suitable for cell culture of the bioreactor chamber (2) are coated with a gel which changes its physicochemical properties with temperature. In a particular example, this gel is poly(n-isopropyl acrylamide). At 37° C., this gel is suitable for cell adhesion and allows the cells to adhere to the surfaces (3, 22, 39) covered by the gel facilitating cell amplification. In a particular example, a gel is not used rather the inner surfaces (3, 22, 39) suitable for cell culture of the bioreactor chamber (2) are adapted to change their properties depending on the temperature to allow cell adhesion.

When cell adhesion has taken place, new culture medium continuously circulates through the device at a temperature such that the inner surface (3, 22, 39) suitable for the culture maintains the physicochemical conditions facilitating cell adhesion, entering, in the particular example shown in FIG. 1, through the medium inlet valve (13) of the pre-chamber (4) and exiting through the medium outlet valves (14, 17, 18, 23). Advantageously, by making the medium flows continuously, the medium is renewed to the conditions required for cell culture.

In one embodiment, the system comprises sensors for oxygen concentration, carbon dioxide concentration, pH and temperature located after the outlet valve (17) for controlling the levels of these variables during the amplification process.

In a particular example as depicted in FIG. 1, a control unit (20) comprising an optical control system (21) is used for controlling the density and the number of cells and to stop the amplification when the target number of cells is reached.

In this embodiment, the device (1) which is placed horizontally in this step of the process has a transparent surface (22); below this transparent surface (22), which can be covered with a gel and on which the cells can therefore adhere and multiply in this step, there is located at least one microscope which measures the number of cells and cell density. This optical microscope transmits this information to the control unit (20) and the system thus works automatically.

Once the target number of cells has been obtained or the cell density reaches a value from which the quality of the culture is lower than that required, the physicochemical conditions of the medium circulating in a continuous flow are changed to modified physicochemical conditions for which the inner surface (3, 22, 39) suitable for cell culture has a physicochemical characteristic such that it allows the cells to again be in suspension in the medium. To that end, once the device (1) has achieved modified physicochemical conditions, for example, a temperature T2 due to the entry of flow at this temperature, the continuous flow of the medium is stopped and it is left to stand in the device (1) until the cells are again in suspension. The liquid medium with the cells in suspension is then transferred to the pre-chamber (4). In the particular example of FIG. 1, when the target number of cells or the maximum density is reached, which are automatically detected in the particular embodiment shown in FIG. 1 by means of the control unit (20) having an optical control system (21), the continuously circulating culture medium is circulated at a temperature T2 long enough so as to allow this temperature to be uniform in the entire device (1). At this temperature the inner surfaces (3, 22, 39) suitable for cell culture have properties that are not suitable for cell adhesion, whereby the cells are again suspended, losing their adhesion to the surface or surfaces suitable for the culture. In a particular example, the culture medium is passed from the outlet of the chamber (7) for containing cell culture medium through transport conduits (9) comprising a heat exchanger (11); thus the temperature changes from T1 to T2.

In a particular example, the temperature T2 is 24° C. since the poly(n-isopropyl acrylamide) gel used in this embodiment behaves such that cell adhesion does not occur at this temperature.

The continuous flow of the medium is then interrupted such that the volume remaining within the device is equal to that of the bioreactor chamber (2) used for amplification, and that this entire volume of the medium at temperature T2 is located in the first bioreactor chamber (2).

When the cells have been separated and are again in suspension in the culture medium, the culture medium with the cells in suspension is transferred to the pre-chamber. In the example of FIGS. 1, 2.1, 2.2, 2.3 and 2.4, the device (1) is rotated, in a particular example, with the help of a mechanism (16) for moving the device (1) in a direction opposite the direction of the preceding step of FIG. 2.3 until reaching the position shown in FIG. 2.4, such that it is in a vertical position, with the second valve (14) at the same level as or lower than the culture medium with the cells in suspension. In this position, and with the help of pressure changes caused by the gas inlet and outlet valves (15, 19) for the entry and exit of a gas, in a particular example, nitrogen, the culture medium with the cells in suspension is transferred to the pre-chamber (4).

If the culture is carried on in the first chamber for obtaining a greater number of total cells, the quality of the culture would decrease as a large number of cells accumulates, sharing a limited growth surface. The advantage provided by the iterative method according to the invention is that the number of cultured cells is increased insofar as more cells are needed, but not at the expense of a density such that the quality of the culture is negatively affected. To that end, a second bioreactor chamber (2') is filled up, which results in a new iteration of the method according to the invention, since the final target number of cells has not been reached and the quality of the cells being amplified in the first bioreactor chamber (2) is affected by the density acquired by the culture medium with the cells. The embodiment of the invention is as described below:

The pre-chamber (4) is filled with an additional amount of culture medium which arrives through the transport conduits (9) from the chamber (7) for containing cell culture medium and enters through the valve (13). This additional amount of culture medium has a volume usually equal to that of the second bioreactor chamber (2'). Therefore, in this step of this embodiment the total volume of culture medium in the pre-chamber (4) is equal to the sum of the capacity of the first bioreactor chamber (2) plus the second bioreactor chamber (2').

The second valve (14) is in a position such that the culture medium with the cells in suspension is located in the pre-chamber (4) at a height equal to or greater than the valve, therefore being able to pass through same. To facilitate the fluid medium transfer between the pre-chamber (4) and the bioreactor chamber (2, 2'), in a particular example, the pre-chamber (4) comprises a gas inlet valve (15) connected to a nitrogen cylinder. The last bioreactor chamber (2"), which in this example is the third bioreactor chamber, comprises a gas outlet valve (19). Therefore, the transfer of the culture medium with the cells in suspension is facilitated by injecting, in this particular case, nitrogen, since it is inert for the cells.

In the embodiment shown in FIG. 1, the bioreactor chambers (2, 2') are in communication by means of a third valve (18) allowing the passage of culture medium between them. In this step of this particular embodiment, when all the culture medium leaves the pre-chamber (4), the bioreactor chambers (2, 2') are filled up.

Once the culture medium with the cells in suspension has been passed to the first bioreactor chamber (2) and to the second bioreactor chamber (2'), the mechanism (16) for moving the device (1) moves the device (1) again to a position such that the second valve (14) between the pre-chamber (4) and the first bioreactor chamber (2) is located, in this particular example, at a height equal to or greater than that of the culture medium with the cells in suspension, and the culture medium is thus located in the bioreactor chambers (2, 2') without the possibility of having an escape route towards the pre-chamber (4).

In a particular embodiment, the first bioreactor chamber (2) and the second bioreactor chamber (2') have a series of additional surfaces for cell adhesion (39) which can be of spherical or tubular shape, among other shapes, so that the surface useful for culture is greater than that allowed by the inner surfaces (3, 22) suitable for cell culture of both bioreactor chambers (2, 2'). In a particular embodiment, to make adhesion possible, the additional surfaces for cell adhesion (39) and the inner surfaces (3, 22) suitable for cell culture of the bioreactor chamber (2, 2') are covered with a gel which changes its properties as a specific physicochemical condition, in this example, the temperature, changes. In a particular example, this gel is a poly(n-isopropyl acrylamide) gel. At 37° C., this gel is such that it allows the cells to adhere to the surfaces (3, 22, 39) covered by the gel, facilitating cell division. In a particular example, a gel is not used rather the inner surfaces (3, 22, 39) suitable for cell culture of the bioreactor chambers (2, 2') are adapted to change their properties depending on the temperature to allow cell adhesion.

When cell adhesion has taken place, new culture medium continuously circulates through the device at a temperature such that the inner surfaces (3, 22, 39) suitable for the culture maintain the physicochemical conditions facilitating cell adhesion, entering, in the particular example shown in FIG. 1, through the medium inlet valve (13) of the pre-chamber (4) and exiting through the medium outlet valve (17) of the last chamber (2") to be filled. Advantageously, by making the medium flows continuously, the medium is renewed to the conditions required for cell culture.

In one embodiment, the system comprises sensors for oxygen concentration, carbon dioxide concentration, pH and temperature located after the outlet valve (17) for controlling the levels of these variables during the amplification process.

In a particular example as depicted in FIG. 1, a control unit (20) comprising an optical control system (21) is used for controlling the density and the number of cells and to stop the amplification when the target level is reached.

In this embodiment, the device (1) which is placed horizontally in this step of the process has a transparent surface (22); below this transparent surface (22), which can be covered with a gel and on which the cells can therefore adhere and multiply in this step, there are located a series of microscopes which measure the number of cells and cell density. These optical microscopes transmit this information to the control unit (20) and the system thus works automatically.

When the density from which the quality of the culture is not the required one or the number of desired cells is reached, which are automatically detected in the particular embodiment shown in FIG. 1 by means of the control unit (20) having an optical control system (21), the continuously circulating culture medium changes the value of the at least one selected initial physicochemical condition, in this example, the temperature, to a temperature T2 long enough so as to allow this temperature to be uniform in the entire device (1). At this temperature the inner surfaces (3, 22, 39) suitable for cell culture have physicochemical properties that are not suitable for cell adhesion, whereby the cells are again suspended, losing their adhesion to the surface or surfaces suitable for the culture. In a particular example, the culture medium is passed from the outlet of the chamber (7) for containing cell culture medium through transport conduits (9) comprising a heat exchanger (11); thus the temperature changes from T1 to T2.

In a particular example, the temperature T1 is 37° C. and the temperature T2 is 24° C. since the poly n-isopropyl acrylamide gel used in this embodiment behaves such that it is suitable for cell adhesion at 37° C. and such that it is not suitable for cell adhesion at 24° C.

The continuous flow of the medium is then interrupted such that the volume remaining within the device is equal to the sum of the volumes of the bioreactor chambers (2, 2') used for amplification, and that this entire volume of the medium at temperature T2 is located in these two bioreactor chambers (2, 2').

Figure 24:
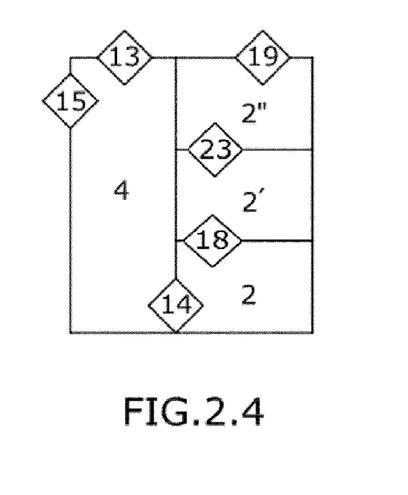

When the cells have been separated and are again in suspension in the culture medium, the device (1) is rotated with the help of the mechanism (16) for moving the device (1), in the particular example of FIG. 1, such that it is located in a vertical position, as indicated in FIG. 2.4, with the second valve (14) at the same level or lower than the culture medium with the cells in suspension. In this position, and with the help of pressure changes caused by the gas inlet and outlet valves (15, 19) for the entry and exit of a gas, in a particular example, nitrogen, the culture medium with the cells in suspension is transferred to the pre-chamber (4).

If the culture is carried on in the first and second chambers for obtaining a greater number of total cells, the quality of the culture would decrease as a large number of cells accumulates, sharing one and the same growth surface. The advantage provided by the iterative method according to the invention is that the number of cultured cells is increased insofar as more cells are needed, but not at the expense of a density such that the quality of the culture is negatively affected. To that end, a third bioreactor chamber (2") is filled up, which results in a new iteration of the method according to the invention. The steps in this example are similar to those described above for filling a bioreactor chamber and for filling two bioreactor chambers, and all the particular embodiments considered are also applicable. Specifically, in the embodiment shown in FIG. 1, the bioreactor chambers (2, 2', 2") are in communication by means of valves (18, 23) allowing the passage of culture medium between them.

In the particular embodiment shown in FIG. 1 comprising three bioreactor chambers, this third bioreactor chamber (2") corresponds to the last bioreactor chamber to be filled, such that it comprises the gas outlet valve (19) and the medium outlet valve (17).

In this particular embodiment, when the culture medium with the cells in suspension is transferred in the manner described above to the pre-chamber (4) through the valves (14, 18, 23), cell culture can no longer be carried on without deterioration in the quality of the culture.

In the embodiment of FIG. 1, once the target number of cells has been reached by means of successively filling up the three aforementioned chambers, the culture medium is transferred from the pre-chamber (4) towards an end outlet valve (24) such that the culture medium leaves the device (1).

In a particular embodiment, the culture medium which is transferred from the device (1) passes through a filtration system (25) in which the cells are separated from the culture medium in the following manner:

In a particular embodiment, the filtration system (25) comprises a chamber (26) for containing liquid medium, such as a buffered liquid, and conduits (27) located between said chamber for containing liquid and the filtration system (25). This filtration system (25) comprises liquid inlet-outlet means and culture medium inlet-outlet means. In both cases, the inlet-outlet means are valves in a particular embodiment. In the particular embodiment of FIG. 1, the culture medium enters the filtration system (25) through a valve (28) and exits the filtration system through the valve (32); the liquid in turn enters the filtration system (25) through a valve (29) and exits the filtration system through a valve (30).

The filtration system (25) internally comprises a filter (31) which, in a particular embodiment, comprises vibrating means (37). The filter (31) retains the cells in suspension in the culture medium; in the corresponding particular embodiment, the cells are separated from the filter (31) by means of the movement caused by the vibrating means (37) in the filter (31). In a particular embodiment, the liquid which enters the filtration system (25) through the valve (29) collects the cells such that the cells are in suspension in the liquid; in this particular embodiment, the liquid, which in a particular embodiment is a buffered liquid, exits the filtration system (25) through the valve (30). Therefore, liquid with a specific cell concentration (concentration C) is found at the outlet of said valve (30). In the particular embodiment of FIG. 1, the culture medium exits the filtration system (25), without cells in suspension, through the valve (32).

In a particular embodiment, the system comprises a sterilization system (33). Specifically, in the particular embodiment shown in FIG. 1, the sterilization system (33) comprises a chamber (34) for containing sterilizing substance, a pump (35) for pumping the sterilizing substance through the transport conduits (9, 10) and a valve (36) regulating the entry of sterilizing substance into the rest of the system.

The invention claimed is:

1. A cell culture method characterized in that it is implemented in a system comprising:
    at least one device suitable for culturing cells, the device comprising:
        at least one bioreactor chamber comprising at least one inner surface suitable for cell culture,
        fluid inlet-outlet means, and
        at least one pre-chamber in connection with the at least one bioreactor chamber, comprising an inlet for introducing cells,
    said method comprising:
    a) filling the pre-chamber with a culture medium under initial physicochemical conditions with a predetermined volume of liquid,
    b) introducing cells in the pre-chamber through the cell inlet,
    c) passing the culture medium with the cells to the at least one bioreactor chamber,
    d) leaving the cells to settle and leaving them to stand for a predetermined time until they adhere to the at least one inner surface suitable for cell culture the physicochemical properties of which cause it to behave in such a way that it favors cell adhesion under one or several initial physicochemical conditions,
    e) circulating culture medium between said at least one bioreactor chamber and said at least one pre-chamber through the fluid inlet-outlet means,
    f) once a target number of cells is obtained or a critical density is reached in the at least one bioreactor chamber used for the culture, changing at least one of the initial physicochemical conditions of the culture medium to modified physicochemical conditions under which cell adhesion is prevented, such that the volume remaining within the device under modified physicochemical conditions is located in the bioreactor chambers which have been used for cell amplification,
    g) passing the culture medium with the cells to the pre-chamber, and
    h) either extracting the culture medium with the cells in suspension through outlet means, if the target number of cells has been reached; or
        introducing additional culture medium in the pre-chamber and repeating the steps starting from step c), if the target number of cells has not been reached.

2. The method according to claim 1, characterized in that the at least one of the initial physicochemical conditions that is changed is the temperature.

3. The method according to claim 1, characterized in that it comprises automatically controlling the number and/or the density of cells by means of at least one control unit suitable for controlling the cell culture carried out in the device.

4. The method according to claim 3, characterized in that the control of the number and/or the density of cells is performed by means of a control unit comprising an optical control system and through a transparent surface comprised in the device, the control of the number of cells comprising:
    once the culture medium has been passed to the at least one bioreactor chamber, positioning the device such that the culture medium with the cells in suspension is located on the transparent surface and this transparent surface is in turn positioned on the optical control system for controlling the number and/or the density of cells.

5. The method according to claim 1, further comprising a step for sterilizing the system by means of a sterilization system connected with said system.

6. The method according to claim 1, characterized in that passing the culture medium to the at least one bioreactor chamber is performed by pressure such that the medium goes through several valves.

7. The method according to claim 1, further comprising separating the cells from the culture medium after extracting the culture medium through outlet means, using a separating system comprising:
    a liquid medium contained in a chamber, and
    at least one filtration system connected to said chamber, which comprises:
        a liquid medium inlet-outlet means,
        a culture medium inlet-outlet means, and
        at least one filter,
    said separating comprising:
        introducing the culture medium with the cells to the filtration system,
        retaining the cells with the at least one filter,
        introducing liquid medium in the filtration system through the liquid medium inlet-outlet means,
        such that the cells are separated from the culture medium.

8. The method according to claim 7, characterized in that the cells are separated from the filter by shaking said filter by means of at least one vibrating means comprised in said filter.

9. The method according to claim 1, characterized in that cultures of different type are prepared by means of a system comprising a plurality of detachable devices, each of these devices using at least one inner surface suitable for the type of culture to be prepared.

10. An iterative cell culture method for obtaining a target number of cultured cells, said method being implemented in a system comprising:
    a device suitable for culturing cells, the device comprising:
    a fluid pathway which circulates a cell culture medium through said device, said fluid pathway having an inlet and an outlet;
    a pre-chamber, comprising a cell inlet,
    a first bioreactor chamber comprising a first inner surface, said first bioreactor chamber being in fluid connection with the pre-chamber through said fluid pathway,
    at least one second bioreactor chamber comprising a second inner surface, said second bioreactor chamber being in fluid connection with the first bioreactor chamber through said fluid pathway, and
    said method comprising:
    a) introducing a liquid culture medium and cells into the pre-chamber;
    b) passing the culture medium with the cells to the first bioreactor chamber;

c) allowing the cells to adhere to the first inner surface under an initial set of physicochemical conditions which favor cell adhesion;
d) culturing cells in the first bioreactor chamber while circulating culture medium between said first bioreactor chamber and the pre-chamber through said fluid pathway;
e) once a critical cell density is reached in the first bioreactor chamber, changing the initial set of physicochemical conditions of the culture medium to modified physicochemical conditions which favor formation of a suspension of cells in the culture medium;
f) passing the culture medium with the cells in suspension to the pre-chamber;
g) determining whether the culture medium of step (f) contains the target number of cells;
h) either:
   extracting the culture medium with the cells in suspension through an outlet means, if the target number of cells has been achieved; or
   increasing the volume of culture medium in the pre-chamber, if the target number of cells has not been achieved; passing the increased volume of culture medium, with the cells in suspension, to the first bioreactor chamber and the at least one second bioreactor chamber; and culturing cells in the first bioreactor chamber and the at least one second bioreactor chamber until both the critical cell density and a target number of cells are obtained.

* * * * *